United States Patent

Neumann

Patent Number: 5,446,971
Date of Patent: Sep. 5, 1995

[54] METHOD FOR THE DIMENSIONAL MEASUREMENT OF WORKPIECES

[75] Inventor: Jan Neumann, Huttenberg, Germany

[73] Assignee: Leitz Messtechnik GmbH, Wetzlar, Germany

[21] Appl. No.: 180,988

[22] Filed: Jan. 14, 1994

[30] Foreign Application Priority Data

Jan. 14, 1993 [DE] Germany .......................... 43 00 762.7
Nov. 10, 1993 [DE] Germany .......................... 43 38 351.3

[51] Int. Cl.$^6$ ............................................. G01D 3/028
[52] U.S. Cl. ....................................... 33/702; 33/503; 33/DIG. 19
[58] Field of Search .................. 33/702, 701, DIG. 19, 33/503; 374/142

[56] References Cited

U.S. PATENT DOCUMENTS

| | | | |
|---|---|---|---|
| 4,895,454 | 1/1990 | Kammleiter et al. | 374/163 |
| 4,949,469 | 8/1990 | Wachtler | 33/702 |
| 4,997,287 | 3/1991 | Tittl | 33/702 |
| 5,031,331 | 7/1991 | Herzog et al. | 33/702 |
| 5,195,826 | 3/1993 | Enderle et al. | 33/702 |

FOREIGN PATENT DOCUMENTS

3620118 12/1987 Germany .
3729644 3/1989 Germany .

OTHER PUBLICATIONS

A. Weckenmann, "Coordinate Measurement Technique in Page Make-Up", Technical Measurement tm, vol. 57, No. 3, 1990, pp. 95-102. (No Translation Provided).

*Primary Examiner*—Christopher W. Fulton
*Attorney, Agent, or Firm*—Foley & Lardner

[57] ABSTRACT

A method for compensating sliding temperature influences on workpieces during a dimensional measurement process. For this purpose, the workpiece temperature and the relative position of the workpiece in relation to the measuring apparatus are recorded at the start and at the end of the actual measurement. By use of the recorded values, the temperature of the workpiece can be calculated at each instant of the dimensional measurement and the relative position of the workpiece in relation to the measuring apparatus and therefore the corrected scanning point can thus be determined. Thus, in the dimensional measurement of workpieces, while taking into account the temperature influences, the temperature straight line in the time interval from the start of measurement to the end of measurement is divided by intermediate measurements into part intervals, within which interpolation can be carried out. For a further improvement of these values, the instants of coordinate measurement are made to coincide with the instants of temperature measurement.

9 Claims, 3 Drawing Sheets

METHOD FOR THE DIMENSIONAL MEASUREMENT OF WORKPIECES

BACKGROUND OF THE INVENTION

The invention relates to a method for compensating sliding temperature influences on workpieces during a measuring process, in which the workpiece is measured at particular points by scanning with a measuring sensor of a measuring apparatus with respect to the absolute zero point of the latter.

According to the state of the art, in dimensional measurements the temperature of the workpiece is determined before the actual measurement, and the linear thermal expansion is taken into account by means of a coefficient of thermal expansion $\alpha$ of the workpiece.

For this purpose, according to DE 3,620,118 A1, a gage is placed next to the workpiece. A conclusion can be drawn as to the workpiece temperature from the change in length of the gage. This method is fairly complicated and laborious. The determination of the temperature of the workpiece therefore takes place only once at the start of the measurement run, on the assumption that the temperature does not change or changes only insignificantly during the further measurement run. A corresponding method is employed in DE 3,729,644 A1, except that, in this publication, a temperature sensor is used instead of the gage. In this method too, the temperature is measured only once at the start of the measurement run. The article by Weckenmann A., "Koordinatenmesstechnik im Umbruch" ("Coordinate measurement technique in page make-up") in the German journal: "Technisches Messen tm" ("Technical Measurement tm"), volume 57, 1990, No. 3, pages 95 to 102, also mentions only different stationary temperatures during a measurement run, that is to say the initial temperature of the workpiece is determined for the entire measurement run, in order then to reckon back the workpiece coordinates, for example in relation to a reference temperature of 20° Celsius.

The disadvantage of these methods belonging to the state of the art is that they assume that the temperature of the workpiece does not change during the dimensional measurement. In longer measurement runs at an initial temperature of the workpiece which differs sharply from the ambient temperature, for example after a washing operation at a temperature of, for example, 60° Celsius, however, it cannot be assumed that the temperature of the workpiece remains unchanged, since it decreases sharply during the measurement run. If an unchanged temperature is nevertheless assumed, measuring errors can occur and can be of the same order of magnitude as the total thermal correction, especially when features measured at the start of the measurement run are linked with features measured at the end of the measurement run.

SUMMARY OF THE INVENTION

One object of the invention is to indicate a measurement method which compensates sliding temperature influences during the measurement process.

In the method according to the invention, the temperature of the workpiece is measured at the start of a dimensional measurement run. The temperature and instant of this measurement are stored, for example in a computer. Immediately thereafter, the relative position of the workpiece in relation to the system of coordinates of the measuring apparatus is recorded (determination of the workpiece system of coordinates). The instant of this measurement is retained.

Subsequently, the dimensional measurement run is executed normally, and at each scan the instant of each individual scan is also stored in addition to the dimensional scanning coordinates.

At the end of the dimensional measurement run, the temperature of the workpiece is measured again, the workpiece system of coordinates is determined and the instant of measurement is retained.

From a knowledge of the temperature-compensating behavior of the workpiece in relation to its environment, the fade-out constant $\tau$ can be determined:

$$\tau = -\frac{t_2 - t_1}{\ln\frac{T_2 - T_u}{T_1 - T_u}}$$

with $T_1$, $T_2$ = workpiece temperatures at the instants $t_1$, $t_2$, $\tau$ = fade-out constant, $(T_1 - T_u)$ = temperature difference between workpiece temperature and ambient temperature $(T_u)$ in the first temperature measurement at the instant $t_1$ before the start of the dimensional measurement run, $(T_2 - T_u)$ = temperature difference between workpiece temperature and ambient temperature $(T_u)$ in the second temperature measurement at the instant $t_2$ after the end of the dimensional measurement run.

The temperature of the workpiece can thus be calculated at each instant of the dimensional measurement run.

The workpiece system of coordinates is likewise determined at the two instants $t_1$ and $t_2$. In a first approximation, this workpiece system of coordinates varies linearly with the temperature, so that it can also be interpolated at each instant $t$ of a scan of the dimensional measurement run.

From a knowledge of the instant of each scan of the dimensional measurement run, a conclusion can be drawn as to the temperature of the workpiece at this instant and as to the position of the workpiece system of coordinates in the system of coordinates of the measuring apparatus. Each scanning point can thus be corrected in relation to an expansion center fixed in the workpiece, for example the origin of the workpiece system of coordinates.

According to one aspect of the invention, therefore, the temperature is determined at the start of the measurement run and at the end of the measurement run and in a diagram is plotted as a straight line through the initial and final temperature values with time as the abscissa and with temperature as the ordinate. The temperature values located between these values are interpolated by means of the time sequence of the measuring operation.

Another object of the invention is to improve this method in terms of its accuracy.

Because the time interval of the measurement run is now subdivided into a plurality of time intervals and the temperature values belonging to these times are determined exactly, the temperature values can each be assumed to be a straight line for a part interval. The straight lines of the part intervals therefore match the exact temperature trend more accurately, so that the temperature corrections of the measured values by interpolation necessarily become more accurate.

Perfectly exact temperature values are obtained at the points at which the instant of coordinate measurement coincides with a temperature measurement. The method indicated can therefore be idealized by executing a temperature measurement at the instant of each coordinate measurement, so that an interpolation of the temperature values becomes completely superfluous.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENTS

Figure 1:
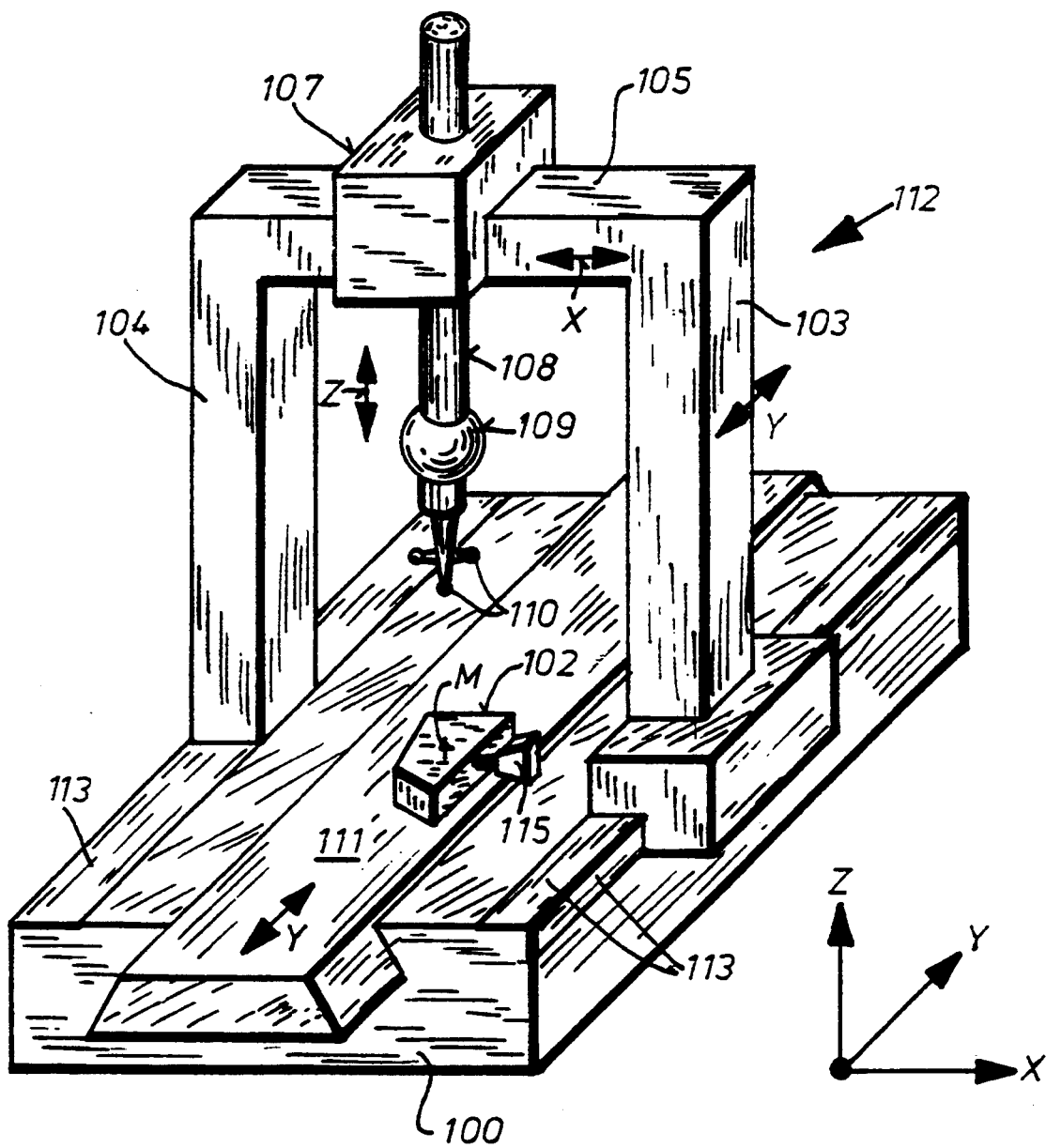
FIG. 1 shows a coordinate measuring machine for practicing the method of the invention.

As shown in FIG. 1, the coordinate measuring machine consists of a bed 100 on which the workpiece 102 that is to be measured is disposed. The supports 103 and 104 for a beam 105 are fastened to bed 100. Parts 103, 104 and 105 are refereed to as portal 112. Component 107 is measurably displaceable in a guide of component 107 in the coordinate direction X. Component 107 bears a spindle sleeve 108 on whose end the measuring head 109 is fastened. The measuring head 109 bears several sensors 110 whose tips can be brought selectively into contact with the workpiece 102 at the measuring point M. To enable a particular measuring point M on the workpiece to be sensed by a sensor 110 the spindle sleeve 108 is measurably displaceable in the direction of the arrow Z.

To determine the coordinates in direction Y, the workpiece 102 that is to be measured is disposed either on a carriage 111 which is displaceable in the bed 100 in the direction of the arrow Y, or no carriage 111 is provided, and instead the workpiece 102 is disposed directly on the bed 100. In this case the portal 112 consisting of the supports 103 and 104 and the beam 105 is measurably displaceable in the direction of the arrow Y, for example in a guide 113 which is provided on both sides of the bed.

To determine the temperature of the workpiece 102, a temperature measuring sensor 115 is provided which contacts the workpiece 102 and measures its temperature. The sensing head 109 bears several sensors 110 which can be brought into the active position selectively in order to be able to sense the workpiece 102 from each side and in any direction and even in cavities not represented.

Figure 2:
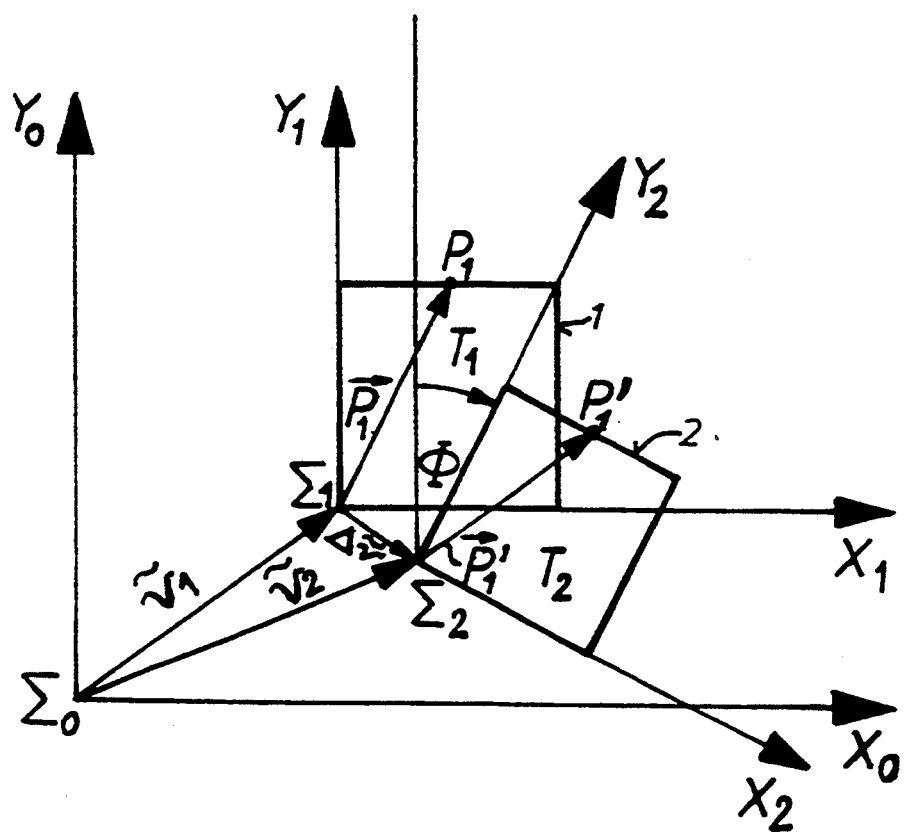
FIG. 2 is a diagram to explain one aspect of the invention.

In FIG. 2, the position and shape of the workpiece 201 are represented in the system of coordinates $\Sigma_0$ with the coordinates $x_0$, $y_0$ of the measuring apparatus, specifically at the start of the dimensional measurement, in the system of coordinates $\Sigma_1$ with the coordinates $x_1$, $y_1$. At the end of the dimensional measurement, the workpiece has assumed the position 202 in the system of coordinates $\Sigma_2$ with the coordinates $x_2$, $y_2$. For the sake of clarity, the problem is treated two-dimensionally. The following considerations also apply unrestrictedly in three-dimensional terms.

The scanning point $P_1$ in the system of coordinates $\Sigma_1$ has travelled to scanning point $P'_1$ at the end of the measurement. The points $P_1$ and $P'_1$ are represented by the vectors $\vec{P}_1$ and $\vec{P}'_1$ in the system of coordinates $\Sigma_1$ and $\Sigma_2$.

During the dimensional measurement and, for example, a simultaneous cooling operation, the workpiece 201, simultaneously contracting, travels out of the position $\Sigma_1$ into the position $\Sigma_2$. In FIG. 2, $\vec{v}$, $\vec{v}_2$ are vectors.

This change in position can be described by rotation through the angle $\Phi$ and the displacement vector $\Delta \vec{v}$. The angle $\Phi$ is to be replaced by the rotation matrix $\hat{\Phi}$ in the three-dimensional case.

The displacement vector $\Delta \vec{v}$ and the angle of rotation $\Phi$ are each assumed to be in proportion to the temperature change $\Delta T$ of the workpiece. The proportionality factors are designated by $\beta_\Phi$ and $\beta_{\vec{v}}$. They are obtained from the temperature measurement before and after the dimensional measurement run and from the workpiece system of coordinates determined at the same time. Thus:

$$\Phi = \beta_\Phi (T_1 - T_2)$$

and $$\vec{v} = \beta_{\vec{v}} (T_1 - T_2).$$

The method is then divided into the following steps:
a) Measurement of the temperature T, of the workpiece and of the ambient temperature $T_u$ at the instant $t_1$, (start of measurement).
b) Determination of the workpiece system of coordinates $\Sigma_1$ at the instant $t_1$.
c) Dimensional measurement of the workpiece with storage of the scanning points and of the instants of the respective scans in relation to the starting instant $t_1$.
d) Measurement of the temperature of the workpiece and of the ambient temperature $T_u$ at the instant $t_2$ (end of the dimensional measurement or end of an interval).
e) Determination of the workpiece system of coordinates $\Sigma_2$ at the instant $t_2$.
f) Calculation of the transform $\Sigma_1 \rightarrow \Sigma_2$ with preparation of the rotation matrix $\hat{\Phi}$ and of the displacement vector $\Delta \vec{v}$.
g) Parametrization of the rotation matrix $\hat{\Phi}$ and of the displacement vector $\Delta \vec{v}$ with the temperature:

$$\hat{\Phi}(T_t) = \begin{bmatrix} \beta_{\Phi 11}(T_1 - T_t) & , & \beta_{\Phi 12}(T_1 - T_t) & , & \beta_{\Phi 13}(T_1 - T_t) \\ \beta_{\Phi 21}(T_1 - T_t) & , & \beta_{\Phi 22}(T_1 - T_t) & , & \beta_{\Phi 23}(T_1 - T_t) \\ \beta_{\Phi 31}(T_1 - T_t) & , & \beta_{\Phi 32}(T_1 - T_t) & , & \beta_{\Phi 33}(T_1 - T_t) \end{bmatrix} = \tilde{\beta}_{\Phi}(T_1 - T_t)$$

$$\Delta \tilde{v}(T_t) = \begin{bmatrix} \beta_{\tilde{v}x}(T_1 - T_t) \\ \beta_{\tilde{v}y}(T_1 - T_t) \\ \beta_{\tilde{v}z}(T_1 - T_t) \end{bmatrix} = \tilde{\beta}\tilde{v}(T_1 - T_t)$$

$\Phi(T_2)$ and $\Delta \tilde{v}$ $(T_2)$ transforming the workpiece system of coordinates $\Sigma_1$ into the workpiece system of coordinates $\Sigma_2$.

h) Determination of the characteristic quantities of the temperature trend according to:

$$(T_2 - T_u) = (T_1 - T_u) \cdot e^{-\frac{t_2 - t_1}{\tau}}$$

with ($T_1 - T_u$) temperature difference between workpiece and environment in the first temperature measurement at the instant $t_1$ before the start of the dimensional measurement run, ($T_2 - T_u$) = temperature difference between workpiece and environment in the second temperature measurement at the instant $t_2$ after the end of the dimensional measurement run, $\tau$ = fade-out constant.

This yields:

$$\tau = -\frac{t_2 - t_1}{\ln \frac{T_2 - T_u}{T_1 - T_u}}$$

i) Correction of each scanning point of the dimensional measurement run by the following sub-steps:
aa) calculation of the temperature $T_t$ of the workpiece at the instant t of the scan according to:

$$T_t = (T_1 - T_u) \cdot e^{-\frac{t - t_2}{\tau}} + T_u.$$

bb) calculation of the rotation matrix $\hat{\Phi}$ ($T_t$) and of the displacement vector $\Delta \tilde{v}$ ($T_t$) for the instant t, cc) transformation of the scanning point by the use of $\hat{\Phi}$ ($T_t$) and $\Delta \tilde{v}$ ($T_t$) into the workpiece system of coordinates $\Sigma_t$ valid at the instant t, dd) execution of the temperature compensation of the scanning point by relating the calculated workpiece temperature $T_t$ to a 20° C. and by relating the scanning coordinates to the expansion center at the origin of the workpiece system of coordinates $\Sigma_t$ at the instant t, k) Evaluation of the corrected scanning points in the known way.

By means of this method, scanning points, which have been measured and recorded at different temperatures of the workpiece, can be related to one another.

In order to increase the accuracy of the method, the measurement of the workpiece temperature and workpiece system of coordinates is advantageously repeated several times during the dimensional measurement run. The intervals to be bridged by interpolation then become smaller.

Figure 3:
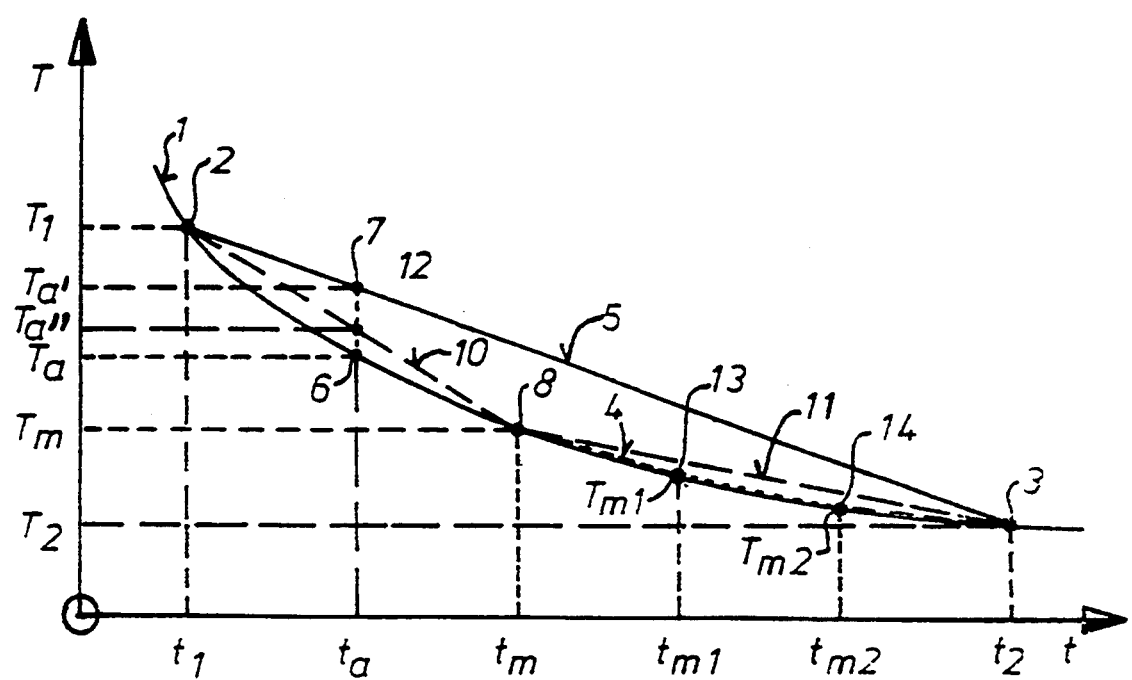
FIG. 3 shows an exemplary embodiment of the invention in the form of a diagram to explain the mode of action.

Turning now to FIG. 3, the time axis is designated by t and the temperature axis by T.

The temperature-trend curve in the diagram is designated by (1) and is represented as an unbroken line.

At the start of the coordinate measurement (instant $t_1$), the temperature $T_1$ is measured. The measuring point (2) is thus fixed on the temperature curve (1).

The time $t_2$ is reached at the end of the measurement run. The temperature $T_2$ belongs to this final time $t_2$, so that the point (3) is obtained on the temperature curve (1) in the diagram. The true temperature-trend curve (1) runs through the points (2 and 3). This is approximated, according to the method described above in relation to FIG. 2, by means of a straight line (5) drawn through the points (2 and 3).

If a coordinate measurement is executed at the instant $t_a$, then the point (6) corresponding to a temperature value $T_a$ is obtained on the temperature-trend curve (1). However, on account of the approximation of the temperature-trend curve (1) obtained by means of the straight line (5), the temperature $T_a'$ is obtained at the point (7) on the straight line (5) and is affected by an error of the amount $T_a'-T_a$. According to the invention, the straight line (5) is approximated by an intermediate measurement at the instant $t_m$ and at the associated temperature $T_m$, in that a straight line (10) (represented by broken lines) is drawn between the points (8 and 2) on the temperature curve (1), and a straight line (11) is drawn between the points (8 and 3). If the measurement is based on a straight line (10), the temperature value $T_a''$ is obtained at the instant $T_a$ and, as can be seen, is substantially closer to the true value $T_a$.

In the right-hand part of the diagram, it is assumed that a co-ordinate measurement takes place at the instant $t_{m1}$ and $t_{m2}$ in each case. The associated temperature values can be determined by means of the curve (11).

In a refinement of the method, there are placed between the points (8 and 3) further interval points (13 and 14) which are assigned to the times $t_{m1}$ and $t_{m2}$ and at which the exact temperature values $T_{m1}$ and $T_{m2}$ have been measured. A further interpolation straight line can be drawn through the points (8 and 13) and also through the further points (13 and 14) as well as (14 and 3). These straight lines already coincide very accurately with the curve (1).

It can be seen that the more time intervals are placed in the temperature range between the times $t_1$ and $t_2$, the more accurate temperature values can be interpolated. And if the interval points (6, 8, 13, 14) are made to coincide with the instants of co-ordinate measurement, that is to say, for example, with the times $t_a$, $t_m$, $t_{m1}$ and $t_{m2}$, then the exact temperature values $T_a$, $T_m$, $T_{m1}$ and $T_{m2}$ are obtained.

How far the subdivision of the diagram is to be taken in the method according to the invention depends on the desired accuracy and on the outlay involved.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A method for a dimensional measurement of a workpiece with a coordinates measuring apparatus while taking into account a thermal change of the workpiece during the measurement, the method comprising the steps of:

measuring a temperature $T_1$ of the workpiece at a start of a dimensional measurement run at time $t_1$, implementing the dimensional measurement run by scanning the workpiece and recording ascertained linear measured values at measuring points $P_i$, recording scanning times $t_i$ of the workpiece at measuring points $P_i$ during the measurement run, measuring a temperature $T_2$ of the workpiece at time $t_2$ on termination of the measurement run, which time $t_2$ is the time of measuring a last point on the workpiece, applying a correction to the measured values at measuring points $P_i$ of the workpiece on the basis of a calculated interpolated temperature $T_i$ at the scanning time $t_i$, ascertaining a thermal expansion of the workpiece on the basis of the calculated/interpolated temperature $T_i$ in time interval $t_1$, $t_2$ and transferring this measured result to the ascertained/measured value at point $P_i$ of the workpiece, whereby a linear interpolation of the temperature $T_i$ in time interval $t_1$, $t_2$ of the measuring operation can be executed.

2. The method as claimed in claim 1, wherein an interval ($t_1$, $T_1$; $t_2$, $T_2$) is divided into at least two part intervals.

3. The method as claimed in claim 2, further comprising the step of executing at least one measurement of the workpiece temperature and of the system of coordinates of the workpiece during the dimensional measurement run, within the interval ($t_1$, $T_1$; $t_2$, $T_2$), in addition to measurements executed before and after the dimensional measurement run.

4. The method as claimed in claim 2, further comprising the following steps:

a) measuring the temperature $T_1$ of the workpiece and of an ambient temperature $T_u$ at the time $t_1$ (start of measurement), b) determining a workpiece system of coordinates $\Sigma_1$ at the time $t_1$, c) dimensionally measuring the scanning points of the workpiece, and storing the scanning points and the times of the respective measurements in relation to the starting time $t_1$, d) measuring the temperature $T_2$ of the workpiece and of the ambient temperature $T_u$ at the time $t_2$ (end of measurement or end of an interval), e) determining a workpiece system of coordinates $\Sigma_u$ at the time $t_2$, f) calculating a transform $\Sigma_1 \rightarrow \Sigma_2$ with a set-up of a corresponding rotation matrix $\hat{\phi}$ and of a corresponding displacement vector $\Delta \vec{v}$, g) parametrization of the rotation matrix $\phi$ and of the displacement vector $\Delta \vec{v}$ with the temperature, h) determining characteristic quantities of a temperature trend according to:

$$(T_2 - T_u) = (T_1 - T_u) \cdot e^{-\frac{t_2 - t_1}{\tau}}$$

with $(T_1 - T_u)$ = temperature difference between workpiece temperature and ambient temperature in the first temperature measurement at the time $t_1$ at the start of the dimensional measurement run, $(T_2 - T_u)$ = temperature difference between workpiece temperature and ambient temperature in the temperature measurement at the time $t_2$ at the end of the dimensional measurement run or of the interval, $\tau$ = fade-out constant of the temperature as a function of time and temperature:

$$\tau = \frac{t_2 - t_1}{\ln \frac{T_2 - T_u}{T_1 - T_u}}$$

i) correcting each scanning point of the dimensional measurement run by performing the following steps:

aa) calculating a temperature $T_t$ of the workpiece at the time t of a scan according to:

$$T_t = (T_1 - T_u) \cdot e^{-\frac{t - t_1}{\tau}} + T_u$$

bb) calculating a rotation matrix $\hat{\phi}$ ($T_t$) and a displacement vector $\Delta \vec{v}$ ($T_t$) for the time t, cc) transforming the scanning point by use of $\hat{\phi}$ ($T_t$) and $\Delta \vec{v}$ ($T_t$), into a workpiece system of coordinates $\Sigma$ valid at the time t, dd) executing a temperature compensation of the scanning point by relating the measured workpiece temperature $T_t$ to 20° Celsius and by relating scanning coordinates to an expansion center at an origin of the workpiece system of coordinates $\Sigma_t$ at the time t, and k) evaluating the scanning points.

5. The method as claimed in claim 1, further comprising the following steps:

a) measuring the temperature $T_1$ of the workpiece and of an ambient temperature $T_u$ at the time $t_1$ (start of measurement), b) determining a workpiece system of coordinates $\Sigma_1$ at the time $t_1$, c) dimensionally measuring the scanning points of the workpiece, and storing the scanning points and the times of the respective measurements in relation to the starting time $t_1$, d) measuring the temperature $T_2$ of the workpiece and of the ambient temperature $T_u$ at the time $t_2$ (end of measurement or end of an interval), e) determining a workpiece system of coordinates $\Sigma_u$ at the time $t_2$, f) calculating a transform $\Sigma_1 \rightarrow \Sigma_2$ with a set-up of a corresponding rotation matrix $\hat{\phi}$ and of a corresponding displacement vector $\Delta \bar{v}$, g) parametrization of the rotation matrix $\hat{\phi}$ and of the displacement vector $\Delta \bar{v}$ with the temperature, h) determining characteristic quantities of a temperature trend according to:

$$(T_2 - T_u) = (T_1 - T_u) \cdot e^{-\frac{t_2-t_1}{\tau}}$$

with
- $(T_1 - T_u)$ = temperature difference between workpiece temperature and ambient temperature in the first temperature measurement at the time $t_1$ at the start of the dimensional measurement run,
- $(T_2 - T_u)$ = temperature difference between workpiece temperature and ambient temperature in the temperature measurement at the time $t_2$ at the end of the dimensional measurement run or of the interval,
- $\tau$ = fade-out constant of the temperature as a function of time and temperature:

$$\tau = \frac{t_2 - t_1}{\ln \frac{T_2 - T_u}{T_1 - T_u}}$$

i) correcting each scanning point of the dimensional measurement run by performing the following steps:

aa) calculating a temperature $T_t$ of the workpiece at the time t of a scan according to:

$$T_t = (T_1 - T_u) \cdot e^{-\frac{t-t_1}{\tau}} + T_u$$

bb) calculating a rotation matrix $\hat{\phi}(T_t)$ and a displacement vector $\Delta \bar{v}(T_t)$ for the time t, cc) transforming the scanning point by use of $\hat{\phi}(T_t)$ and $\Delta \bar{v}(T_t)$, into a workpiece system of coordinates $\Sigma_t$ valid at the time t, dd) executing a temperature compensation of the scanning point by relating the measured workpiece temperature $T_t$ to 20° Celsius and by relating scanning coordinates to an expansion center at an origin of the workpiece system of coordinates $\Sigma_t$ at the time t, and k) evaluating the scanning points.

6. A method for a dimensional measurement of a workpiece, while taking into account external temperature influences on the workpiece during the measurement, by measuring the temperature of the workpiece before the dimensional measurement and by taking into account a linear thermal expansion by use of a coefficient of thermal expansion of the workpiece, the method comprising the steps of:

measuring, at a start of a dimensional measurement run, a temperature $T_1$ of the workpiece at an instant $t_1$ and recording a relative position of the workpiece in relation to a system of coordinates of a measuring apparatus a first time, wherein the dimensional measurement run is executed by recording a number of scanning points;

measuring, at an end of the dimensional measurement run, a temperature $T_2$ of the workpiece at an instant $t_2$ and recording the relative position of the workpiece in relation to the system of coordinates a second time; and correcting each individual scanning point of the dimensional measurement run with respect to an instant of measurement in an interval ($t_1$, $t_2$), the method further comprising the following steps:

a) measuring the temperature $T_1$ of the workpiece and of an ambient temperature $T_u$ at the instant $t_i$ (start of measurement), b) determining a workpiece system of coordinates $\Sigma_1$ at the instant $t_1$, c) dimensionally measuring the scanning points of the workpiece, and storing the scanning points and the instants of the respective measurements in relation to the starting instant $t_1$, d) measuring the temperature $T_2$ of the workpiece and of the ambient temperature $T_u$ at the instant $t_2$ (end of measurement or end of an interval), e) determining a workpiece system of coordinates $\Sigma_u$ at the instant $t_2$, f) calculating a transform $\Sigma_1 \rightarrow \Sigma_2$ with a set-up of a corresponding rotation matrix $\hat{\phi}$ and of a corresponding displacement vector $\Delta \bar{v}$, g) parametrization of the rotation matrix $\hat{\phi}$ and of the displacement vector $\Delta \bar{v}$ with the temperature, h) determining characteristic quantities of a temperature trend according to:

$$(T_2 - T_u) = (T_1 - T_u) \cdot e^{-\frac{t_2-t_1}{\tau}}$$

with
- $(T_1 - T_u)$ = temperature difference between workpiece temperature and ambient temperature in the first temperature measurement at the instant $t_1$ at the start of the dimensional measurement run,
- $(T_2 - T_u)$ = temperature difference between workpiece temperature and ambient temperature in the temperature measurement at the instant $t_2$ at the end of the dimensional measurement run or of the interval,
- $\tau$ = fade-out constant of the temperature as a function of time and temperature:

$$\tau = \frac{t_2 - t_1}{\ln \frac{T_2 - T_u}{T_1 - T_u}}$$

i) correcting each scanning point of the dimensional measurement run by performing the following steps:

aa) calculating a temperature $T_t$ of the workpiece at the instant t of a scan according to:

$$T_t = (T_1 - T_u) \cdot e^{-\frac{t-t_1}{\tau}} + T_u$$

bb) calculating a rotation matrix $\hat{\phi}(T_t)$ and a displacement vector $\Delta \bar{v}(T_t)$ for the instant t, cc) transforming the scanning point by use of $\hat{\phi}(T_t)$ and $\Delta \bar{v}(T_t)$, into a workpiece system of coordinates $\Sigma$ valid at the instant t, dd) executing a temperature compensation of the scanning point by relating the measured workpiece temperature $T_t$ to 20° Celsius and by relating scanning coordinates to an expansion center at an origin of the workpiece system of coordinates $\Sigma$ at the instant t, and k) evaluating the scanning points.

7. A method for a dimensional measurement of a workpiece, while taking into account external temperature influences on the workpiece during the measurement, by measuring the temperature of the workpiece before the dimensional measurement and by taking into account a linear thermal expansion by use of a coefficient of thermal expansion of the workpiece, the method comprising the steps of:

measuring, at a start of a dimensional measurement run, a temperature $T_1$ of the workpiece at an instant $t_1$ and recording a relative position of the workpiece in relation to a system of coordinates of a measuring apparatus a first time, wherein the dimensional measurement run is executed by recording a number of scanning points;

measuring, at an end of the dimensional measurement run, a temperature $T_2$ of the workpiece at an instant $t_2$ and recording the relative position of the workpiece in relation to the system of coordinates a second time; and correcting each individual scanning point of the dimensional measurement run with respect to an instant of measurement in an interval $(t_1, t_2)$, wherein an interval $(t_1, T_1; t_2, T_2)$ is divided into at least two part intervals, the method further comprising the following steps:
a) measuring the temperature $T_1$ of the workpiece and of an ambient temperature $T_u$ at the instant $t_1$ (start of measurement),
b) determining a workpiece system of coordinates $\Sigma_1$ at the instant $t_1$,
c) dimensionally measuring the scanning points of the workpiece, and storing the scanning points and the instants of the respective measurements in relation to the starting instant $t_1$,
d) measuring the temperature $T_2$ of the workpiece and of the ambient temperature $T_u$ at the instant $t_2$ (end of measurement or end of an interval),
e) determining a workpiece system of coordinates $\Sigma_u$ at the instant $t_2$,
f) calculating a transform $\Sigma_1 \rightarrow \Sigma_2$ with a set-up of a corresponding rotation matrix $\hat{\phi}$ and of a corresponding displacement vector $\Delta \bar{v}$,
g) parametrization of the rotation matrix $\hat{\phi}$ and of the displacement vector $\Delta \bar{v}$ with the temperature,
h) determining characteristic quantities of a temperature trend according to:

$$(T_2 - T_u) = (T_1 - T_u) \cdot e^{-\frac{t_2-t_1}{\tau}}$$

with $(T_1 - T_u)$ = temperature difference between workpiece temperature and ambient temperature in the first temperature measurement at the instant $t_1$ at the start of the dimensional measurement run, $(T_2 - T_u)$ = temperature difference between workpiece temperature and ambient temperature in the temperature measurement at the instant $t_2$ at the end of the dimensional measurement run or of the interval, $\tau$ = fade-out constant of the temperature as a function of time and temperature:

$$\tau = \frac{t_2 - t_1}{\ln \frac{T_2 - T_u}{T_1 - T_u}}$$

i) correcting each scanning point of the dimensional measurement run by performing the following steps:
aa) calculating a temperature $T_t$ of the workpiece at the instant t of a scan according to:

$$T_t = (T_1 - T_u) \cdot e^{-\frac{t-t1}{\tau}} + T_u$$

bb) calculating a rotation matrix $\hat{\phi}$ $(T_t)$ and a displacement vector $\Delta v$ $(T_t)$ for the instant t,
cc) transforming the scanning point by use of $\hat{\phi}$ $(T_t)$ and $\Delta v$ $(T_t)$, into a workpiece system of coordinates $\Sigma_t$ valid at the instant t,
dd) executing a temperature compensation of the scanning point by relating the measured workpiece temperature $T_t$ to 20° Celsius and by relating scanning coordinates to an expansion center at an origin of the workpiece system of coordinates $\Sigma_t$ at the instant t, and k) evaluating the scanning points.

8. A method for a dimensional measurement of a workpiece with a coordinates measuring apparatus while taking into account a thermal change of the workpiece during the measurement, by measuring the temperature of the workpiece before the dimensional measurement and by taking into account a linear thermal expansion by use of a coefficient of thermal expansion of the workpiece, comprising the steps of:

recording, at a start of a dimensional measurement run, a temperature $T_1$ of the workpiece at an instant $t_1$ and recording a first time a relative position of the workpiece in relation to a system of coordinates of a measuring apparatus;

subsequently executing the dimensional measurement run with a number of scanning points being recorded;

measuring, at an end of the dimensional measurement run, a temperature $T_2$ of the workpiece at an instant $t_2$ and recording a second time the relative position of the workpiece in relation to the system of coordinates;

correcting each individual scanning point of the dimensional measurement run in relation to the instant of measurement in an interval $t_1$, $t_2$; and executing and evaluating at least one measurement of workpiece temperature and of the workpiece system of coordinates during the dimensional measurement run, within an interval $t_1$, $T_1$; $t_2$, $T_2$, in addition to measurements executed before and after the dimensional measurement run;

wherein the at least one additional measurement of the temperature and of the workpiece system of coordinates is executed during the measurement run at the instant of a measurement of the coordinates of the workpiece.

9. The method as claimed in claim 8, wherein all additional measurements of the workpiece temperature are executed at the instant or at least approximately at the instant of all respective measurements of the coordinates of the workpiece.

* * * * *